Figure 1:
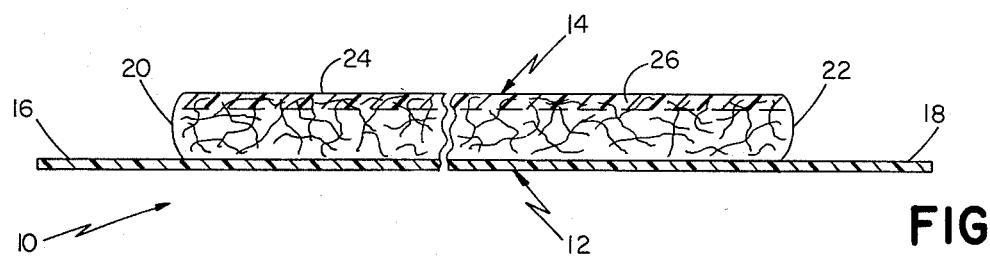

United States Patent [19]

Schaar

[11] 4,050,463
[45] Sept. 27, 1977

[54] DIAPERS

[75] Inventor: Charles H. Schaar, Lake Zurich, Ill.

[73] Assignee: Colgate-Palmolive Company, New York, N.Y.

[21] Appl. No.: 716,094

[22] Filed: Aug. 20, 1976

[51] Int. Cl.² .............................................. A61F 13/16
[52] U.S. Cl. .................................... 128/287; 128/284; 128/290 P; 128/296
[58] Field of Search ............... 128/284, 287, 290 R, 128/290 P, 296; 428/290, 212, 317, 218

[56] References Cited

U.S. PATENT DOCUMENTS

| | | | |
|---|---|---|---|
| 3,111,948 | 11/1963 | Burgeni | 128/290 R |
| 3,395,201 | 7/1968 | Kalwaites | 128/290 R |
| 3,523,536 | 8/1970 | Ruffo | 128/287 |
| 3,626,944 | 12/1971 | Schaar | 128/287 |
| 3,661,680 | 5/1972 | Gore | 128/287 |
| 3,663,348 | 5/1972 | Lilola | 128/284 X |
| 3,721,242 | 3/1973 | Krusko | 128/287 |
| 3,750,669 | 8/1973 | DeLuca | 128/287 |
| 3,759,775 | 9/1973 | Shepherd | 428/290 |
| 3,765,418 | 10/1973 | Jones, Sr. | 128/287 |
| 3,828,783 | 8/1974 | Kennette et al. | 128/284 |
| 3,848,594 | 11/1974 | Buell | 128/284 |
| 3,848,597 | 11/1974 | Endres | 128/287 |
| 3,848,598 | 11/1974 | Mesek | 128/287 |
| 3,852,007 | 7/1974 | Rand | 128/296 |
| 3,863,637 | 2/1975 | MacDonald | 128/287 |
| 3,884,234 | 5/1975 | Taylor | 128/287 |
| 3,901,238 | 8/1975 | Gellert | 128/287 |
| 3,903,890 | 9/1975 | Mesek | 128/287 |
| 3,952,124 | 4/1976 | Mesek | 428/218 |
| 3,955,577 | 5/1977 | Gellert | 128/290 R |

Primary Examiner—Aldrich F. Medbery

[57] ABSTRACT

In a disposable diaper comprising a porous absorbent pad of cellulosic fibers and a water impervious back sheet adjacent and bonded to one surface of the pad, that improvement wherein the fibers at the surface of the pad opposite the backing sheet are bonded together with a resinous material, the bonded fibers forming a porous matrix defining the top layer of the diaper and being adapted for placement in direct contact with the infant's skin.

10 Claims, 2 Drawing Figures

DIAPERS

This invention relates to disposable diapers.

The usual multi-layer disposable diaper includes a water impervious back sheet or outer layer, a highly absorbent pad for retaining body fluids such as urine, and a top sheet or inner layer intended for placement in direct contact with an infant's skin. The absorbent pad is typically a batt of loosely compacted cellulosic fibers having little structural strength or integrity, but capable of absorbing relatively large quantities of liquid. The top sheet is less hydrophylic than the pad, but has greater structural strength and surface integrity.

In the finished diaper, liquid deposited on the top surface should quickly flow into and be absorbed by the pad, and the top surface should remain relatively dry and should not shed or otherwise disintegrate. To date, satisfactory accomplishing of these goals has required that the diaper include a separate top sheet and absorbent pad.

Accordingly, it is a principal object of the present invention to provide a disposable diaper in which the need for a separate top sheet is eliminated. Other objects include providing such a diaper which is cheaper to manufacture than are disposable diapers now available, and in which the upper surface of the pad is treated to provide the desired surface strength and integrity, and absorbtion and surface dryness characteristics.

The invention features, in a disposable diaper comprising a porous absorbent pad of cellulosic fibers and a water impervious back sheet adjacent and bonded to one surface of the pad, that improvement wherein the fibers at the surface of the pad opposite the backing sheet are bonded together with a resinous material, the bonded fibers forming a porous matrix defining the top layer of the diaper and being adapted for placement in direct contact with the infant's skin. In preferred embodiments in which the binder extends from the pad upper surface inwardly a distance not more than 25% of the overall thickness of the pad, the binder includes a resin selected from the group consisting of acrylic, alkyd, polyurethane and vinyl, and the pad has a basis weight in the range of 0.025 to 0.050 grams per square centimeter, a density under a compression of 2.1 $g/cm^2$ in the range of 0.065 to 0.140 g/cc, and a density under a compression of 51.2$g/cm^2$ in the range of 0.105 to 0.210 g/cc. The preferred embodiments are made by applying the binder on one surface of the pad in liquid or powder form, and then curing the binder by direct application of heat and pressure.

Figure 2:
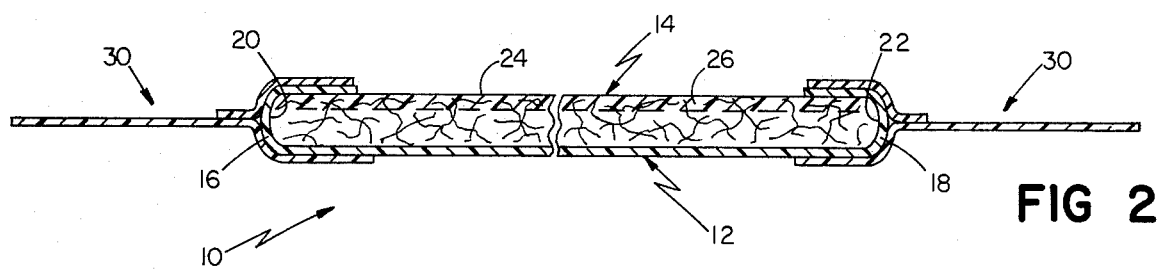

Other objects, features and advantages will appear from the following detailed description of a preferred embodiment of the invention, taken together with the attached drawings in which:

FIG. 1 is a sectional view of a partially-manufactured diaper embodying the present invention; and, FIG. 2 is a sectional view of the completed diaper of FIG. 1.

Referring more particularly to the drawings, there is shown a disposable diaper, generally designated 10, and including a water impervious back sheet 12 and a highly absorbent pad 14. Back sheet 12 and pad 14 itself are of conventional construction, well-known in the art. Typically, the back sheet is of polyethylene, about 1 mil thick, and is embossed or otherwise textures to provide the desired feel or hand. Pad 14 is a batt of loosely compacted cellulosic fibers, such as wood pulp fiber or cotton fibres, or a mixture thereof. The cellulose fibers are primarily held together by interfiber bonds, thus forming a coherent web of low bulk density. The weight per unit area (basis weight) and weight per unit volume (density) of the pad as initially manufactured will vary depending on the type of diaper in which the pad will be used. Overnight diapers, for example, typically have higher basis weights and densities than do diapers intended for daytime use. Typically, the pad will have a density in the range of about 0.065 grams per cubic centimeter to 0.140 grams per cubic centimeter under the slight compression of 2.1 grams per square centimeter, a density in the range of 0.105 to 0.210 grams per cubic centimeter under the greater compression of 51.2 grams per cubic centimeter, and a basis weight in the range of 0.025 to 0.050 grams per square centimeter. In some embodiments, the pad may include a layer of wadding covering the back surface of the fibrous web, between the web and the back sheet.

Pad 14 and back sheet 12 are bonded together as a unit by lines of heat sealing or adhesive, as is known in the art. As shown, the width of backing sheet 12 is greater than that of pad 14, so that the lateral margins 16, 18 of the backing sheet initially extend beyond the lateral edges 20, 22 of the pad.

According to the present invention, the top surface 24 of pad 14 is covered with a resinous binder material. The binder, which is uniformly applied to surface 24, impregnates the fibers of the pad from surface 24 inwardly into the pad. The depth of impregnation is less than 50% of the overall depth of pad 14 and, preferably, less than 25%. When cured, the resinous binder bonds the cellulosic fibers at and adjacent surface 24 together into a net-like structure, forming a smooth, strong, porous skin 26 at the top surface 24 of the pad. If an especially smooth upper surface is desired, the binder is cured under simultaneous application of heat and pressure, typically by passing the pad directly from the point at which the binder is applied to and between a pair of calendar rolls at least the upper one of which, in contact with the resin-applied surface, is heated.

Typically, the resinous bonding material is applied to pad 14 before the pad and back sheet 12 are attached together. In some circumstances, however, it may prove desirable to place pad 14 on, or secure it to, the back sheet 12 before applying the binder to pad upper surface 24.

After the binder has been applied, the lateral margins 16, 18 of the back sheet are folded around and over the respective laterial edges 20, 22 of pad 14 and secured to the top side edge portions of the pad as shown in FIG. 2. Adhesive fastening tapes 30, typically of the type shown in my copending application Ser. No. 410,375, filed Oct. 29, 1973, are then attached to the lateral edges to form a finished diaper.

As will be apparent, any of a wide range of resinous binders may be used in the practice of the present invention. Typical materials include acrylic, alkyd, butyl, vinyl and urethane resins. The binders may be either thermoplastic or thermosetting, depending on the manner in which the binder is to be applied to the pad and on the manner in which the coated surface of the pad is to be cured and finished. Similarly, the binder may be applied to the pad in a variety of different ways. Generally, it will be applied to the pad in liquid form, either by spraying or coating.

The amount of binder applied will depend on the particular formulation and, to a lesser extent, on the manner in which it is applied and cured. Whatever the formulation and method of application and curing, the final resin-bonded fiber surface should be porous, relatively smooth and non-tacky. Additionally, it should have the structural integrity required to resist tearing and shedding when wet.

Since most resinous materials are somewaht hydrophobic, the binder may include a surfactent or other wetting agent, as required to insure that urine and other fluids relatively quickly will flow from the resin-bonded surface into the unbonded fibers in the lower portion of pad 14 (i.e., the so-called strike-through time of the diaper will be relatively short), and, at the same time, that the hydrophobic qualities of the bonded surface will discourage flow of liquid in the opposite direction, thereby causing the liquid to be retained in the absorbent pad and imparting to the finished diaper the desired surface dryness.

Other embodiments of the invention will be within the scope of the following claims.

What is claimed is:

1. In a disposable diaper for contact with the body skin comprising a highly porous absorbent pad of cellulosic fibers and a water-impervious backing sheet adjacent and bonded to one side of said pad, that improvement wherein:
    the fibers of said pad at the surface thereof opposite said backing sheet are bonded together with a resinous binder, said binder and said fibers bonded thereby forming a porous matrix and defining the top body contacting surface of said diaper.

2. The diaper of claim 1 wherein said binder extends from said upper surface inwardly into said pad a distance not more than 50% of the thickness of said pad.

3. The diaper of claim 2 wherein said distance is not more than 25% of said thickness.

4. The diaper of claim 1 wherein said binder comprises a resin selected from the group consisting of acrylic, alkyd, butyl, urethane, and vinyl resins.

5. The diaper of claim 1 wherein the basis weight of said pad is in the range of about 0.150 to 0.210 grams per square centimeter, the density thereof under a compression of 2.1 g/cm² is in the range of 0.065 to 0.140 g/cc., and the density thereof under a compression of 51.2 g/cm² is in the range of 0.105 to 0.210 g/cm².

6. The diaper of claim 1 wherein lateral side edge portions of said backing sheet are folded over and around respective lateral side edges of said pad and adhered to said bonded fibers defining said top surface.

7. The method of making a diaper comprising the steps of providing a pad of absorbent cellulosic fibers, creating a smooth but highly porous body skin contacting top surface on said pad by applying a resinous binder to a first surface of the pad, bonding said fibers together into a net like skin structure by applying heat and pressure to cure the resinous binder, bonding a liquid impervious sheet to the opposite side of said pad, and folding lateral side portions of said backing around and over the lateral edges of said pad and securing said side portions to said bonded surface along said lateral edges whereby said sheet and said first surface define, respectively, the bottom and top surface of said diaper.

8. The method of claim 7 wherein said binder is applied to said first surface in liquid form and including the step of curing said binder by direct application of heat and pressure to said first surface.

9. The method of claim 7 wherein said binder includes a resin selected from the group consisting of alkyd, acrylic, urethane, butyl, and vinyl resins.

10. The method of claim 7 wherein said binder is applied to said first surface in the form of a liquid and penetrates said pad to a distance of not more than 25% of the thickness thereof.

* * * * *